(12) United States Patent
Nakasone et al.

(10) Patent No.: US 7,875,165 B2
(45) Date of Patent: Jan. 25, 2011

(54) METHOD OF CORRECTING OUTPUT OF NOX SENSOR

(75) Inventors: Osamu Nakasone, Frankfurt am Main (DE); Yuichi Sasaki, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 416 days.

(21) Appl. No.: 12/132,213

(22) Filed: Jun. 3, 2008

(65) Prior Publication Data
US 2008/0237064 A1    Oct. 2, 2008

Related U.S. Application Data

(63) Continuation of application No. PCT/JP2007/054255, filed on Mar. 6, 2007.

(30) Foreign Application Priority Data

Mar. 15, 2006    (JP) .............................. 2006-071068

(51) Int. Cl.
G01N 27/407    (2006.01)

(52) U.S. Cl. ................. 205/781; 204/406; 204/425; 73/23.31; 701/103; 702/24

(58) Field of Classification Search ............... 205/781, 205/784; 204/406, 425; 73/23.31; 701/103, 701/114; 702/24, 182
See application file for complete search history.

(56) References Cited

U.S. PATENT DOCUMENTS 5,249,453 A    10/1993    Usami et al.
5,289,717 A    3/1994    Ishida
6,071,393 A *    6/2000    Oshima et al. ............. 204/425
6,284,112 B1    9/2001    Kato et al.
6,355,152 B1    3/2002    Kato et al.
2003/0106808 A1*    6/2003    Miyata et al. ............. 205/761

FOREIGN PATENT DOCUMENTS

| EP | 0 678 740 | 6/2001 |
|---|---|---|
| JP | 4-80653 | 3/1992 |
| JP | 4-204246 | 7/1992 |
| JP | 06-273381 | 9/1994 |
| JP | 08-271476 | 10/1996 |
| JP | 11-237362 | 8/1999 |
| JP | 2000-28576 | 1/2000 |

OTHER PUBLICATIONS

Bosch LSU 4 information, LSU 4 part #0 258 006 066, http://www.techedge.com.au/vehicle/wbo2/2v0/Isu4.htm, Apr. 3, 2003, pp. 1-2.

* cited by examiner

*Primary Examiner*—Kaj K Olsen
(74) *Attorney, Agent, or Firm*—Burr & Brown

(57) ABSTRACT

A method of correcting an output of a NOx sensor including: a first step of obtaining a sensor-variation relational expression based on a relationship between an Ip2/Ip0 value and an output change percentage for a calibration sensor; a second step of obtaining, from the relational expression, an output change percentage β that corresponds to an Ip2/Ip0 value of a subject NOx sensor; a third step of calculating a pressure correction coefficient α based on the obtained β; and a fourth step of performing output correction on the subject NOx sensor by calculating the pumping current $Ip2(p_o)$ under a reference pressure based on the pumping current $Ip2(p)$ and a pressure p of the measurement gas which are detected upon measurement of the NOx concentration in the measurement gas.

12 Claims, 3 Drawing Sheets

US 7,875,165 B2

METHOD OF CORRECTING OUTPUT OF NOx SENSOR

This application is a continuation of the International Application No. PCT/JP2007/054255 filed on Mar. 6, 2007, which claims the benefit under 35 U.S.C. §119(a)-(d) of Japanese Application No. 2006-071068 filed on Mar. 15, 2006, the entireties of which are incorporated herein by reference.

BACKGROUND OF THE INVENTION

1. Field of the Invention

The present invention relates to a method of correcting an output of a NOx sensor, and more particularly to a method of correcting changes in the output of the NOx sensor that arise from output variations in individual NOx sensors and pressure fluctuations of a measurement gas, thereby ensuring a highly accurate sensor output.

2. Discussion of Related Art

There have been proposed various measuring methods and devices for detecting concentrations of NOx components, such as NO and $NO_2$, contained in a measurement gas such as vehicular exhaust emissions. For instance, there is known a NOx sensor element configured to obtain the concentration of the NOx component in the measurement gas by reducing or decomposing the NOx component in the measurement gas and measuring an amount of oxygen generated by reduction or decomposition of the NOx component. Further, a NOx sensor equipped with such a sensor element is also known.

In JP-A-8-271476 (Patent Document 1), JP-A-11-237362 (Patent Document 2), and JP-A-2000-28576 (Patent Document 3), for instance, there is disclosed a sensor element for obtaining the concentration of the NOx component contained in the measurement gas. The sensor element has a laminar structure formed by laminating a plurality of solid electrolyte layers each having a suitable thickness integrally on each other. Within the laminar-structured element, there are provided a first internal space into which the measurement gas is introduced through a first diffusion controlling passage, a second internal space into which an atmosphere in the first internal space is introduced through a second diffusion controlling passage and in which the NOx component existing in the atmosphere is reduced or decomposed, main oxygen pumping means to control an oxygen partial pressure in the first internal space, measurement oxygen pumping means to pump out the oxygen in the second internal space, and current detecting means to detect a pumping current flowing upon a pumping action of the measurement oxygen pumping means. On the basis of a pumping current (a limiting current) detected by the current detecting means, an amount of the NOx component is detected.

The NOx sensor described above undesirably suffers from a problem that the NOx concentration obtained from an output of the NOx sensor (sensor output) does not coincide with an actual NOx concentration in the measurement gas in an instance where the pressure of the measurement gas fluctuates. More specifically explained, when the pressure of the measurement gas increases, the sensor output increases, so that the NOx concentration higher than the actual NOx concentration is detected. On the other hand, when the pressure of the measurement gas is lowered, the sensor output decreases, so that the sensor output to be obtained is lower than the actual NOx concentration in the measurement gas.

In the light of the above, an empirical formula is conventionally found on the basis of relationship of output changes of NOx sensor with respect to pressure of measurement gas (Bosch LSU 4 Information, LSU 4 part #0 258 006 066; Non-Patent Document 1). On the basis of such an empirical formula, the NOx concentration in the measurement gas under a reference pressure (generally an atmospheric pressure) is calculated.

In the meantime, the NOx sensor is mass-produced so as to have a construction similar to each other for use on automotive vehicles and the like. However, outputs from a large number of NOx sensors are not always identical with each other. That is, it is known that the outputs from the respective NOx sensors vary or fluctuate even under the same measurement condition due to subtle differences in the construction and the size among the NOx sensors. To eliminate such output variations among the individual NOx sensors, it is required to examine, for each of the individual NOx sensors, output changes relative to the pressure fluctuation of the measurement gas for obtaining the above-indicated empirical formula (correction formula) and to correct, based on the formula, an output value every time when the NOx concentration in the measurement gas is measured, for thereby obtaining the actual NOx concentration in the measurement gas.

However, it is quite troublesome and costly to examine, for each of a large number of produced NOx sensors, output changes with respect to the pressure of the measurement gas for obtaining the correction formula for each sensor and to correct the output value of each sensor when the NOx concentration in the measurement gas is actually measured. Thus, such an arrangement is not practically feasible.

Patent Document 1: JP-A-8-271476
Patent Document 2: JP-A-11-237362
Patent Document 3: JP-A-2000-28576
Non-Patent Document 1: home page;
Bosch LSU 4 Information, LSU 4 part #0 258 006 066

SUMMARY OF THE INVENTION

The present invention has been made in view of the situations described above. It is therefore an object of the invention to provide a method of easily performing output correction on a NOx sensor with high accuracy. It is also an object of the invention to provide a method of correcting an output of a NOx sensor by effectively correcting changes in the sensor output that arise from pressure fluctuation of a measurement gas while eliminating variations among individual NOx sensors, thereby ensuring highly accurate sensor output.

FORMS OF THE INVENTION

The present invention is preferably carried out in various forms described below to solve the above-indicated problem or problems to be recognized from an entirety of the present description and drawings. It is to be understood that the following forms may be employed in any arbitrary combination. It is to be understood that forms or technical features of the present invention are not limited to those described below but are recognized based on the invention concept described in the entirety of the present description and disclosed in the drawings.

(1) A method of correcting an output of a NOx sensor configured to measure a NOx concentration in a measurement gas, by controlling, to a constant value, an oxygen partial pressure in the measurement gas introduced into a first internal space from a measurement-gas space owing to a pumping action based on a pumping current Ip0 supplied to main oxygen pumping means, introducing a controlled atmosphere in the first internal space into a second internal space for reduction or decomposition of NOx in the atmosphere, and pumping out oxygen generated upon the reduction or the decomposition from the second internal space by measurement oxygen pumping means, so as to measure the NOx concentration in the measurement gas based on a pumping current Ip2 flowing through the measurement oxygen pumping means, the method being characterized by comprising:

a first step of obtaining a sensor-variation relational expression, wherein: the pumping current Ip0 and the pumping current Ip2 are measured for an appropriate number of the NOx sensors each as a calibration sensor using a standard gas, under a reference pressure, whose NOx concentration is already known, for calculating an Ip2/Ip0 value for each of the calibration sensors; an output change percentage is calculated as a ratio of change of a pumping current flowing through the measurement oxygen pumping means obtained in each of the calibration sensors using the standard gas under a prescribed specific pressure different from the reference pressure, to a pumping current flowing through the measurement oxygen pumping means obtained in each of the calibration sensors using the standard gas under the reference pressure; and the sensor-variation relational expression is obtained from a relationship between the Ip2/Ip0 value and the output change percentage for said each of the calibration sensors;

a second step of obtaining an output change percentage $\beta$ for a subject NOx sensor which is different from the calibration sensors and whose output is to be corrected, by calculating, for the subject NOx sensor, the Ip2/Ip0 value using the standard gas under the reference pressure so as to obtain, from the sensor-variation relational expression, the output change percentage $\beta$ that corresponds to the calculated Ip2/Ip0 value;

a third step of calculating a pressure correction coefficient $\alpha$ based on the output change percentage $\beta$ obtained in the second step, according to the following formula (I):

$$\alpha(p'-p_0)/p' = \beta(\beta+1) \quad (I)$$

wherein $p_0$ represents the reference pressure and $p'$ represents the specific pressure of the standard gas; and a fourth step of performing output correction on the subject NOx sensor, wherein: a NOx concentration in the measurement gas is measured using the subject NOx sensor to detect a pumping current $Ip2(p)$ flowing through the measurement oxygen pumping means while a pressure p of the measurement gas is detected; and a pumping current $Ip2(p_0)$ flowing through the measurement oxygen pumping means under the reference pressure $p_0$ is calculated based on the pumping current $Ip2(p)$ and the pressure p, according to the following formula (II):

$$[Ip2(p_0)-Ip2(p)]/Ip2(p) = \alpha(p_0-p)/p \quad (II)$$

so as to perform the output correction on the subject NOx sensor.

(2) The method according to the form (1), wherein the sensor-variation relational expression in the first step is obtained as a linear expression.

(3) The method according to the form (1) or (2), wherein the reference pressure is an atmospheric pressure.

(4) The method according to any one of the forms (1) to (3), wherein the standard gas contains the NOx in concentrations of from 100 ppm to 1000 ppm.

(5) The method according to any one of the forms (1) to (4), wherein the specific pressure is a pressure that falls within a pressure fluctuation range of the measurement gas.

(6) The method according to any one of the forms (1) to (5), wherein each of the main oxygen pumping means and the measurement oxygen pumping means is constituted by an electrochemical cell including a solid electrolyte and a pair of electrodes disposed adjacent thereto.

(7) The method according to any one of the forms (1) to (6), wherein the NOx sensor includes a sensor element in which the main oxygen pumping means and the measurement oxygen pumping means are provided integrally with the first and second internal spaces.

(8) The method according to any one of the forms (1) to (7), wherein the measurement oxygen pumping means includes: an inner pumping electrode which is formed inside of the second internal space and which reduces or decomposes the NOx contained in the atmosphere introduced from the first internal space, as a result of contact with the atmosphere; and an outer pumping electrode formed outside of the second internal space, the measurement oxygen pumping means performing a pumping action with respect to oxygen generated by reduction or decomposition of the NOx contained in the atmosphere introduced from the first internal space, based on a pumping current flowing between the inner and outer pumping electrodes.

(9) The method according to the form (8), wherein the inner pumping electrode formed in the second internal space is covered with a porous layer formed thereon, and an atmosphere in the second internal space is brought into contact with the inner pumping electrode through the porous layer under a prescribed diffusion resistance.

(10) The method according to any one of the forms (1) to (9), wherein the NOx sensor is provided with an auxiliary oxygen pumping means which includes a pair of auxiliary pumping electrodes respectively formed inside and outside of the second internal space, the auxiliary oxygen pumping means performing a pumping action with respect to oxygen contained in the atmosphere introduced from the first internal space, based on an auxiliary pumping current flowing between the pair of auxiliary pumping electrodes.

(11) The method according to the form (10), wherein the auxiliary oxygen pumping means is constituted by an electrochemical cell in which the pair of auxiliary pumping electrodes are formed on a solid electrolyte.

(12) The method according to the form (10) or (11), wherein the NOx sensor includes a sensor element in which the auxiliary oxygen pumping means is provided integrally with the main oxygen pumping means, the measurement oxygen pumping means, and the first and second internal spaces.

EFFECT OF THE INVENTION

In short, the present invention has been completed based on the findings that the Ip2/Ip0 values in the respective NOx sensors and the output change percentages in those sensors have a constant relationship and can be represented by a prescribed sensor-variation relational expression. Based on the Ip2/Ip0 value of the subject NOx sensor whose output is to be corrected, the output change percentage $\beta$ that corresponds to the Ip2/Ip0 value is obtained from the sensor-variation relational expression. Subsequently, the pressure correction coefficient $\alpha$ is obtained from the output change percentage $\beta$, thereby completing the above-indicated formula (II) as an empirical formula relating to the output correction in accordance with the pressure, for use as a correction formula. Further, the pumping current flowing through the measurement oxygen pumping means obtained upon actual measurement of the NOx concentration in the measurement gas and the pressure of the measurement gas are detected, and the output correction is performed on the subject NOx sensor based on the detected values according to the above-indicated correction formula.

In each of the NOx sensors which are mass-produced for various applications, the above-indicated pumping current values Ip0 and Ip2 are measured for the standard gas whose NOx concentration is already known, to detect the NOx concentration in the actual measurement gas based on the relationship between the output value of each NOx sensor and the NOx concentration. In the present invention, the two pumping current values obtained by using the standard gas are utilized, namely, the ratio Ip2/Ip0 is calculated. The output change percentage β of the subject NOx sensor whose output is to be corrected can be obtained according to the sensor-variation relational formula obtained beforehand. Further, the pressure correction coefficient α which completes the correction formula (empirical formula) for calculating the NOx concentration can be obtained.

According to the present method of correcting the NOx sensor output, the pumping current values Ip0 and Ip2 are utilized which are obtained in output-value inspections performed on all of the NOx sensors using the standard gas whose NOx concentration is already known. Further, the Ip2/Ip0 value of the subject NOx sensor is calculated and the output change percentage β of the subject NOx sensor that corresponds to the calculated Ip2/Ip0 value is determined from the sensor-variation relational formula which is obtained beforehand, whereby the pressure correction coefficient α of the subject NOx sensor is calculated. Further, based on the above-indicated formula (II) which is a known empirical formula, the output correction can be easily performed on the subject NOx sensor. Accordingly, the present method completely eliminates a need of obtaining, in advance, an output change curve by measuring the NOx concentrations under different pressure values for all of the NOx sensors.

According to the present invention, by obtaining, in advance, the sensor-variation relational formula, the sensor output of the subject NOx sensor can be easily and effectively corrected in accordance with the pressure fluctuation of the measurement gas while eliminating variations among the individual sensors. Thus, the NOx concentration can be detected with high accuracy.

DETAIL DESCRIPTION OF THE PREFERRED EMBODIMENT

To further clarify the present invention, the present invention will be hereinafter described in detail referring to a representative example of a NOx sensor to which the present invention is applied.

Figure 1:
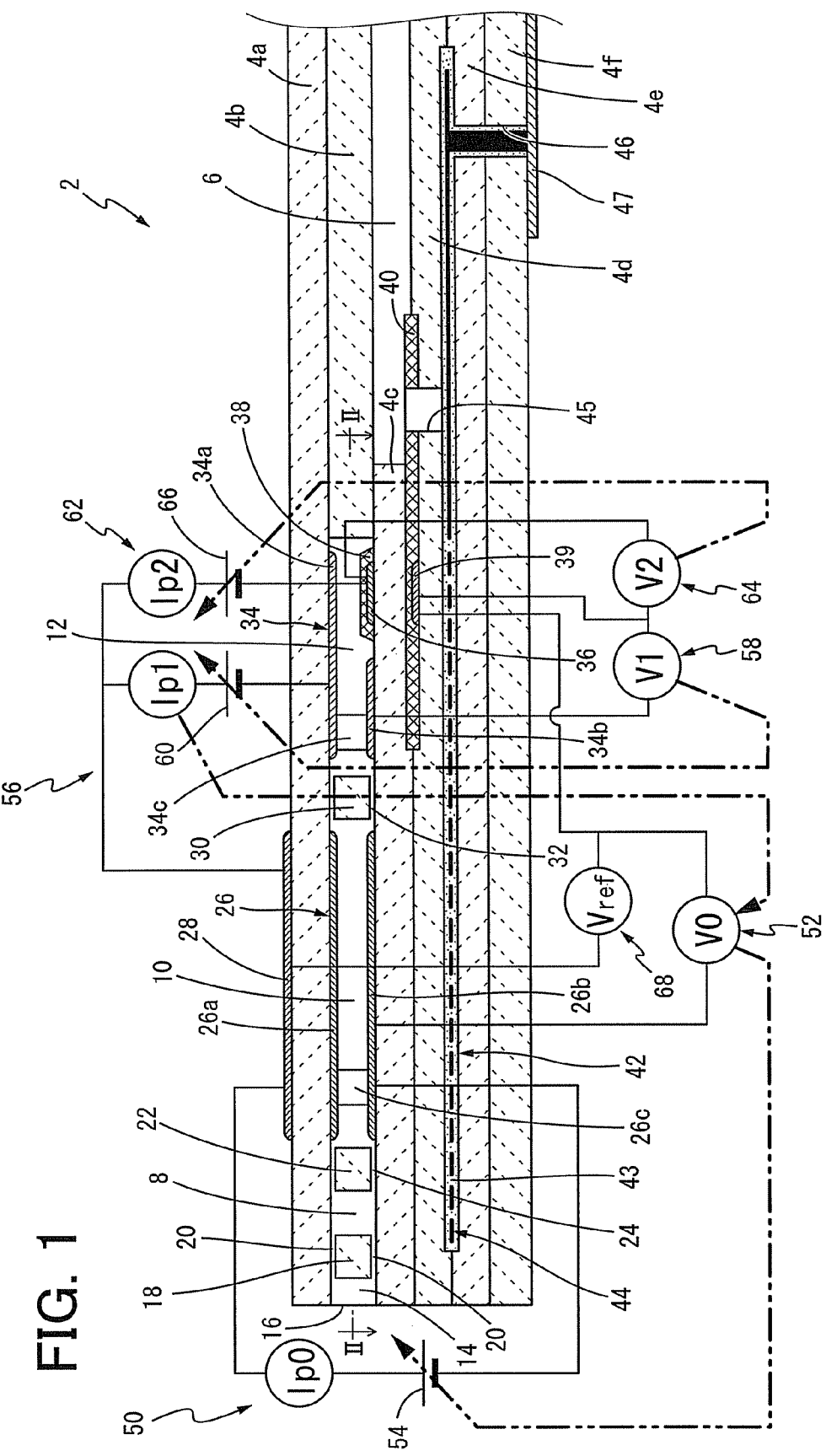
FIG. 1 is an elevational view in longitudinal cross section showing one embodiment of a sensor element used for a NOx sensor to which the output correcting method of the invention is applied.
Figure 2:
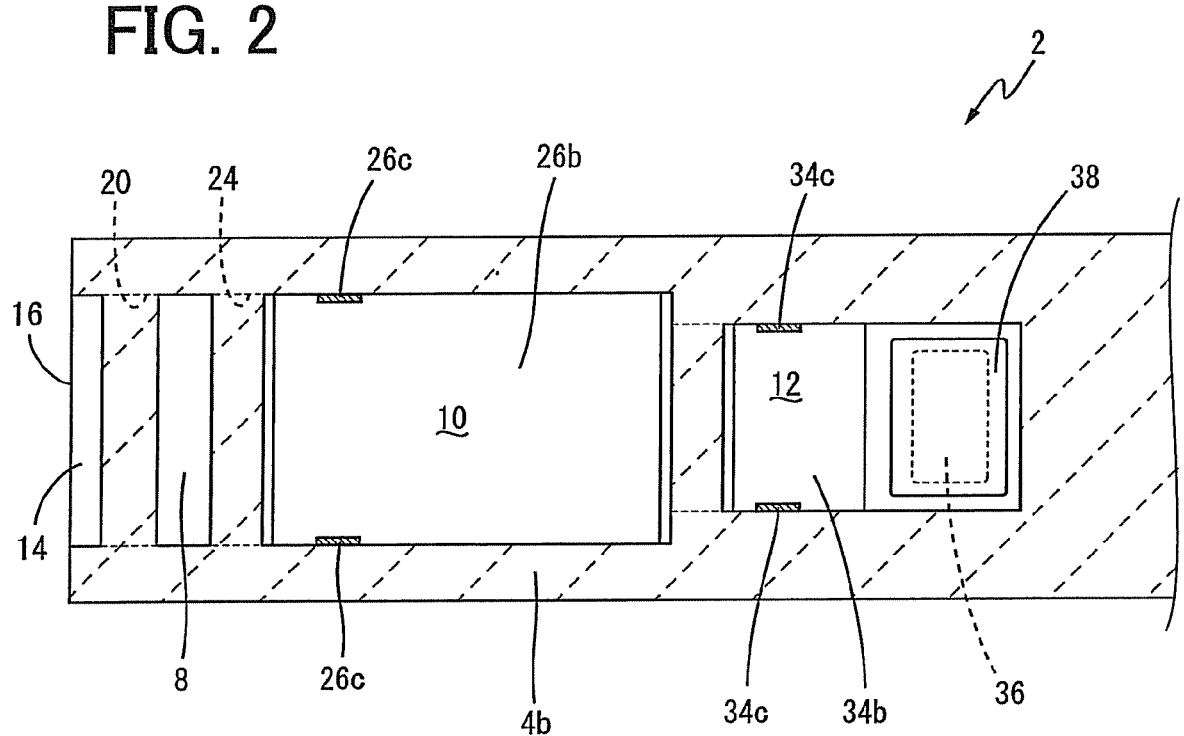
FIG. 2 is a scaled-down partial cross-sectional view taken along line II-II in FIG. 1.

FIGS. 1 and 2 schematically show a construction of the representative example of a NOx (nitrogen oxide) sensor element that constitutes a NOx sensor to which the output correcting method according to the invention is applied. FIG. 1 is a view showing a laminar structure of the element in longitudinal cross section. FIG. 2 is a cross-sectional view of the element taken along line II-II in FIG. 1.

The sensor element indicated at 2 in these figures has a generally elongate plate-like shape with a relatively small width and a relatively large length. As shown in FIG. 1, the sensor element 2 has a laminar structure which includes dense and air-tight oxygen-ion conductive solid electrolyte layers 4a, 4b, 4c, 4d, 4e, and 4f which are laminated on each other so as to provide an integral structure. The solid electrolyte layers 4a-4f are formed of a known oxygen-ion conductive solid electrolyte material such as zirconia ceramics. The integral sensor element 2 is easily produced by firing a laminar structure of unfired solid electrolyte layers, as know in the art.

In the integral sensor element 2, an uppermost solid electrolyte layer 4a and a third solid electrolyte layer 4c from the top in FIG. 1 are laminated on each other with a spacer layer in the form of the solid electrolyte layer 4b being interposed therebetween, thereby defining internal spaces which are located between the solid electrolyte layers 4a, 4c and which have a height corresponding to the thickness of the solid electrolyte layer 4b. In other words, as shown in FIG. 1, the internal spaces in which the solid electrolyte layer 4b does not exist are formed between the solid electrolyte layers 4a, 4c so as to extend in a longitudinal direction of the sensor element 2. The sensor element 2 further has a reference-air introducing passage 6 as a reference-gas space which is formed between the solid electrolyte layers 4b, 4d independently of the internal spaces described above. The reference-air introducing passage 6 in which the solid electrolyte layer 4c does not exist is formed so as to extend in the longitudinal direction of the sensor element 2. As known in the art, the reference-air introducing passage 6 is open to the atmosphere at a proximal end of the sensor element 2.

As shown in FIGS. 1 and 2, the internal spaces formed between the two solid electrolyte layers 4a, 4c in the sensor element 2 include a buffer space 8, a first internal space 10, and a second internal space 12 which are formed independently of each other and arranged in the order of description in the longitudinal direction of the sensor element 2. The buffer space 8 and the first and second internal spaces 10, 12 have rectangular shapes and predetermined width dimensions in plan view. Further, a clogging-preventive space 14 is formed at a distal end of the sensor element 2 so as to be located between the two solid electrolyte layers 4a, 4c with a height corresponding to the thickness of the solid electrolyte layer 4b, like the buffer space 8 and the first and second internal spaces 10, 12. The clogging-preventive space 14 in which the solid electrolyte layer 4b as the spacer layer does not exist is open outward, and the open end of the clogging-preventive space 14 is made as a gas inlet 16 through which a measurement gas existing in an external space outside the sensor element 2 is introduced.

The clogging-preventive space 14 and the buffer space 8 are separated from each other by a first partition wall 18 provided by a portion of the solid electrolyte layer 4b. The first partition wall 18 cooperates with the solid electrolyte layers 4a, 4c which are respectively located on upper and lower sides of the first partition wall 18, to define slits at upper and lower portions of the partition wall 18, respectively. The slits have a width substantially equal to that of the buffer space 8 and extend in a width direction of the element. The slits function as first diffusion controlling passages 20, 20 each as first diffusion controlling means. The measurement gas existing in the external space outside the sensor element 2 which has been introduced into the clogging-preventive space 14 through the gas inlet 16 is introduced into the buffer space 8, under a prescribed diffusion resistance, through the first diffusion controlling passages 20, 20 formed on the upper and lower sides of the first partition wall 18.

The buffer space 8 and the first internal space 10 are separated from each other by a second partition wall 22 provided by a portion of the solid electrolyte layer 4b. Like the first partition wall 18, the second partition wall 22 cooperates with the solid electrolyte layers 4a, 4c which are respectively located near to and remote from the external space, to define slits at upper and lower portions of the second partition wall 22, respectively. The slits that extend in the width direction of the element function as second diffusion controlling passages 24, 24 each as second diffusion controlling means. An atmosphere (measurement gas) existing in the buffer space 8 is introduced into the first internal space 10, under a prescribed diffusion resistance, through the second diffusion controlling passages 24, 24. The sensor element 2 has main pumping means (main oxygen pumping means) which is an electrochemical pumping cell constituted by the solid electrolyte layer 4a, an inner pumping electrode 26 and an outer pumping electrode 28 formed on respective inner and outer surfaces of the solid electrolyte layer 4a. By a pumping action of the main pumping means, oxygen in an atmosphere in the first internal space 10 is pumped out into the external space outside the sensor element 2, or oxygen in the external space is pumped into the first internal space 10, whereby an oxygen concentration (oxygen partial pressure) in the atmosphere in the first internal space 10 is controlled to a prescribed value, e.g., a low concentration at which the NOx is not decomposed or reduced, as known in the art.

In the element structure described above, the provision of the buffer space 8 and the provision of the slit-like first and second diffusion controlling passages 20, 24 respectively for the first and second partition walls 18, 22 that define the buffer space 8 offer the following advantages. That is, oxygen usually enters abruptly an internal space of the sensor element 2 through the gas inlet 16 due to pulsation of the exhaust gas pressure generated in the measurement gas in the external space. In the arrangement, however, the oxygen in the external space is not directly introduced into the internal space (processing space) of the sensor element 2, but is introduced first into the buffer space 8 through the first diffusion controlling passages 20 and then into the first internal space 10 through the second diffusion controlling passages 24. Accordingly, an abrupt change in the oxygen concentration due to the pulsation of the exhaust gas pressure is absorbed or canceled by the buffer space 8 and the first and second diffusion controlling passages 20, 24 between which the buffer space 8 is disposed, so that an influence of the pulsation of the exhaust gas pressure with respect to the internal space (the first internal space 10) can be substantially ignored, resulting in an improvement in correlation between the oxygen pumping amount by the pumping means in the processing space and the oxygen concentration in the measurement gas. The arrangement not only improves the measuring accuracy, but also makes it possible to use the internal space as a sensor for detecting an air/fuel ratio. For obtaining the advantages described above, each of the first and second diffusion passages 20, 24 provided for the respective first and second partition walls 18, 22 are made as the slits each in the form of a clearance of 10 μm or smaller.

The clogging-preventive space 14 formed at the distal end portion of the sensor element 2 so as to be open to the external space is provided for preventing clogging of the buffer space 8 at its inlet end with particulate matters (such as soot and oil combustion residue) contained in the measurement gas which is introduced into the buffer space 8 from the external space through the gas inlet 16. Owing to the clogging-preventive space 14, it is possible to measure the NOx component with higher accuracy for a long time period. Thus, the clogging-preventive space 14 is advantageously provided in the sensor element 2.

In the main pumping means (main oxygen pumping means) disposed in the first internal space 10, the inner and outer pumping electrodes 26, 28 are generally porous cermet electrodes which are formed of a material consisting of a metal such as Pt and a ceramic material such as $ZrO_2$. In particular, the inner pumping electrode 26 disposed in the first internal space 10 and exposed to the measurement gas needs to be formed of a material which does not cause a change of the NOx component in the measurement gas, namely, a material having a lowered ability or no ability to reduce or decompose the NOx component such as NO or $NO_2$. For instance, the inner pumping electrode 26 is formed of a compound having a perovskite structure such as $La_3CuO_4$, a cermet material consisting of a metal such as Au having a low catalytic activity and a ceramic material, or a cermet material consisting of a metal such as Au having a low catalytic activity, a metal of the platinum (Pt) group, and a ceramic material.

As shown in FIG. 1, the inner pumping electrode 26 of the main pumping means is formed over the solid electrolyte layers 4a, 4b, 4c which define the first internal space 10. More specifically described, a ceiling electrode portion 26a of the inner pumping electrode 26 is formed over a portion of the lower surface of the solid electrolyte layer 4a which gives a ceiling surface of the first internal space 10. A bottom electrode portion 26b of the inner pumping electrode 26 is formed over a portion of the upper surface of the solid electrolyte layer 4c which gives a bottom surface of the first internal space 10. Further, lateral electrode portions 26c of the inner pumping electrode 26 are respectively formed over portions of the respective lateral surfaces (inner surfaces) of the solid electrolyte layer 4b which give respective lateral wall portions of the first internal space 10. The lateral electrode portions 26c connect the ceiling electrode portion 26a and the bottom electrode portion 26b. Thus, the inner pumping electrode 26 has a tunnel-like electrode structure in which the inner pumping electrode 26 has a tunnel-like shape at a location where the lateral electrode portions 26c are disposed.

In the illustrated sensor element 2, the first internal space 10 and the second internal space 12 are separated from each other by a third partition wall 30 provided by a portion of the solid electrolyte layer 4b. Like the above-described first and second partition walls 18, 22, the third partition wall 30 cooperates with the solid electrolyte layers 4a, 4c to define slits at upper and lower portions of the third partition wall 30, respectively, as shown in FIG. 1. The slits which extend in the width direction of the element and which have a length substantially equal to the width of the second internal space 12 function as third diffusion controlling passages 32, 32 each as third diffusion controlling means through which the first internal space 10 and the second internal space 12 communicate with each other. The atmosphere which exists in the first internal space 10 and whose oxygen concentration (partial pressure) has been controlled is introduced into the second internal space 12 through the third diffusion controlling passages 32 under a prescribed diffusion resistance.

Within the second internal space 12, there are provided an auxiliary pumping electrode 34 and a measuring electrode 36. The auxiliary pumping electrode 34 cooperates with the solid electrolyte layer 4a and a suitable outer electrode, e.g., the outer pumping electrode 28, to constitute an auxiliary electrochemical pumping cell (an auxiliary oxygen pumping means), thereby controlling the oxygen concentration (partial pressure) in the atmosphere within the second internal space 12 to a prescribed value. The auxiliary pumping electrode 34 is disposed in the second internal space 12 so as to have a tunnel-like electrode structure similar to that of the inner pumping electrode 26 disposed in the first internal space 10. That is, a ceiling electrode portion 34a of the auxiliary pumping electrode 34 is formed over a portion of the lower surface of the solid electrolyte layer 4a that gives a ceiling surface of the second internal space 12. A bottom electrode portion 34b of the auxiliary pumping electrode 34 is formed over a portion of the upper surface of the solid electrolyte layer 4c that gives a bottom surface of the second internal space 12. Lateral electrode portions 34c of the auxiliary pumping electrode 34 which connect the ceiling electrode portion 34a and the bottom electrode portion 34b are formed over portions of the respective lateral surfaces of the solid electrolyte layer 4b that give respective lateral walls of the second internal space 12. Like the inner pumping electrode 26 of the main pumping means described above, the auxiliary pumping electrode 34 is formed of a material having a lowered ability or no ability to cause reduction or decomposition of the NOx component contained in the measurement gas. For instance, the auxiliary pumping electrode 34 is a porous cermet electrode of $Pt—ZrO_2$ containing 1% of Au.

The measuring electrode 36 disposed in the second internal space 12 needs to be formed of a material that includes a component capable of causing reduction or decomposition of the NOx component in the atmosphere which exists in the second internal space 12 and whose oxygen concentration (partial pressure) has been controlled. That is, the component of the material of the measuring electrode 36 needs to cause reduction or decomposition of the NOx component as a result of contact with the atmosphere. Here, the measuring electrode 36 is a porous electrode formed of a cermet material consisting of an electrode metal material capable of reducing or decomposing the NOx component in the measurement gas and a ceramic material. As the electrode metal material of the cermet material of which the measuring electrode 36 is formed, a noble metal is advantageously employed. In particular, platinum (Pt) or an alloy of platinum and rhodium (Rh) is advantageously employed. The ratio of Pt and Rh (Pt:Rh) in the alloy is preferably 100-40 wt %:0-60 wt %. Where the noble metal is used for the electrode metal material, the ratio (vol %) of the noble metal and the ceramic material (the noble metal/the ceramic material) is advantageously held in a range of 65/35-40/60.

As the ceramic material which is another component of the cermet material of which the measuring electrode 36 is formed, a $ZrO_2$ material is advantageously used for ensuring that the measuring electrode 36 is firmly fixed to the solid electrolyte layer 4c.

As shown in FIG. 1, the measuring electrode 36 disposed in the second internal space 12 is covered with a porous ceramic layer as an electrode-protective layer 38 formed of a ceramic material such as $Al_2O_3$ and having a predetermined thickness. The electrode-protective layer 38 is for preventing inert components such as a metal vaporized from the auxiliary pumping electrode 34 disposed in the second internal space 12 from adhering to the measuring electrode 36, thereby effectively keeping the catalytic activity (NOx decomposing/reducing ability) of the measuring electrode 36.

In the illustrated sensor element 2, a reference electrode 39 is disposed on one of opposite sides of the solid electrolyte layer 4c which is remote from the second internal space 12, so as to be exposed to the reference air in the reference-air introducing passage 6. The reference electrode 39 is utilized in measuring the oxygen concentrations (partial pressures) in the atmospheres in the first internal space 10 and the second internal space 12 as well as the oxygen concentration (partial pressure) in the atmosphere (measurement gas) in the external space. In particular, where oxygen-partial-pressure detecting means as an electrochemical sensor cell is constituted by the measuring electrode 36, the solid electrolyte layers 4c, 4d, and the reference electrode 39, it is possible to detect an electromotive force that corresponds to a difference between the amount of oxygen generated by reduction or decomposition of the NOx component contained in the atmosphere surrounding the measuring electrode 36 and the amount of oxygen contained in the reference air, whereby the concentration of the NOx component in the measurement gas can be obtained. The reference electrode 39 which is formed on the solid electrolyte layer 4d as a seal layer is covered with a porous alumina layer 40 through which the reference air existing in the reference-air introducing passage 6 reaches and contacts the reference electrode 39.

As apparent from the above description, the sensor layer of the sensor element 2 is constituted by the solid electrolyte layers 4a-4d, the internal spaces 6, 8, 10, 12, 14, the electrodes 26, 28, 34, 36, 39, and the porous alumina layer 40.

In the sensor element 2, a plurality of ceramic layers in the form of the solid electrolyte layers 4d-4f are laminated on one side of the solid electrolyte layer 4c which is remote from the internal spaces (8, 10, 12), as shown in FIG. 1. Further, a heater layer 42 is interposed between the two adjacent solid electrolyte layers 4d, 4e so as to be enclosed by the same 4d, 4e. The heater layer 42 is configured to generate heat with an electric power supplied from an external power source. The heater layer 42 is provided to heat the solid electrolyte layers 4a-4f that constitute the sensor element 2 to a prescribed temperature for increasing the oxygen ion conductivity of the solid electrolyte layers 4a-4f. The heater layer 42 includes a heater element 44 and an electrically insulating layer 43 which is formed of alumina or the like for ensuring electrical insulation from the solid electrolyte layers 4d, 4e and which encloses the heater element 44. The heater layer 42 is held in communication with the reference-air introducing passage 6 at the proximal end portion of the sensor element 2, through a pressure-releasing hole 45 that is formed through the solid electrolyte layer 4d, whereby an increase in the internal pressure in the heater layer 42 is mitigated. The heater element 44 of the heater layer 42 is pulled out on the element surface via a through-hole 46 which is formed through the solid electrolyte layers 4e, 4f and an inner periphery of which is electrically insulated from the solid electrolyte layers 4e, 4f. Further, the heater element 44 is brought into conduction with a connector pad 47 which is formed so as to be insulated from the solid electrolyte layer 4f.

The heater element 44 of the heater layer 42 is configured to heat, to the prescribed temperature, at least portions of the solid electrolyte layers 4a-4c that define the first internal space 10 and the second internal space 12. As shown in FIG. 2, the heater element 44 is constituted by a heat generating portion 44a for heating the portions of the solid electrolyte layers 4a-4c in the vicinity of the first and second internal spaces 10, 12, and current-supplying lead portions 44b, 44b which are connected to respective ends of the heat generating portion 44a and through which a prescribed heater current is supplied to the heat generating portion 44a. The heater element 44 is sandwiched by and between an upper insulating layer 43a and a lower insulating layer 43b that constitute the electrically insulating layer 43, whereby the heater element 44 is enclosed by the electrically insulating layer 43, as shown in FIG. 1. As the electric current supplied to the heat generating portion 44a of the heater element 44 through the current-supplying lead portions 44b, there may be suitably employed a pulse current having a predetermined frequency at which a predetermined voltage is applied.

In the NOx sensor element 2 described above, the solid electrolyte layer 4a, and the inner and outer pumping electrodes 26, 28 cooperate with each other to constitute an electrochemical pumping cell, namely, a main pumping cell 50 as the main oxygen pumping means. Further, the solid electrolyte layers 4a-4d, and the inner pumping electrode 26, and the reference electrode 39 cooperate with each other to constitute an electrochemical sensor cell, namely, an oxygen-partial-pressure detecting cell 52 (i.e., second oxygen-partial-pressure detecting means) for controlling the main pumping cell 50, to detect the oxygen concentration (partial pressure) in the first internal space 10. Reference numeral 54 denotes a variable power source for driving the main pumping cell 50.

The solid electrolyte layer 4a, the outer pumping electrode 28, and the auxiliary pumping electrode 34 cooperate with each other to constitute an electrochemical pumping cell, namely, an auxiliary pumping cell 56 as the auxiliary oxygen pumping means for controlling the oxygen partial pressure in the atmosphere in the second internal space 12. Further, the solid electrolyte layers, 4a, 4b, 4c, 4d, the auxiliary pumping electrode 34, and the reference electrode 39 cooperate with each other to constitute an electrochemical sensor cell, namely, an oxygen-partial-pressure detecting cell 58 (i.e., third oxygen-partial-pressure detecting means) for controlling the auxiliary pumping cell 56, to detect the oxygen partial pressure in the second internal space 12. The auxiliary pumping cell 56 is driven by a variable power source 60 the voltage of which is controlled by the oxygen-partial-pressure detecting cell 58. A pumping current Ip1 of the auxiliary pumping cell 56 is used to control an electromotive force V0 of the oxygen-partial-pressure detecting cell 52.

The solid electrolyte layers 4a, 4b, 4c, the outer pumping electrode 28, and the measuring electrode 36 cooperate with each other to constitute an electrochemical pumping cell, namely, a measurement pumping cell 62 as a measurement oxygen pumping means for pumping out oxygen generated by decomposition of the nitrogen oxide (NOx) contained in the atmosphere surrounding the measuring electrode 36, to detect an amount of the oxygen generated. The solid electrolyte layers 4a, 4b, 4c, 4d, the measuring electrode 36, and the reference electrode 39 cooperate with each other to constitute an electrochemical sensor cell, namely, an oxygen-partial-pressure detecting cell 64 (fourth oxygen-partial-pressure detecting means) for controlling the measurement pumping cell 62, to detect the oxygen partial pressure in the atmosphere surrounding the measuring electrode 36. The measurement pumping cell 62 is driven by a variable power source 66 the voltage of which is controlled on the basis of an electromotive force V2 detected by the oxygen-partial-pressure detecting cell 64. A pumping current Ip2 of the measurement pumping cell 62 which corresponds to the concentration of the nitrogen oxide contained in the measurement gas is thus obtained.

The solid electrolyte layers 4a, 4b, 4c, 4d, the outer pumping electrode 28, and the reference electrode 39 cooperate with each other to constitute an electrochemical sensor cell 68 (first oxygen-partial-pressure detecting means). An electromotive force Vref obtained by the sensor cell 68 is used to detect the oxygen partial pressure (concentration) in the measurement gas existing in the external space outside the sensor.

The concentration of the nitrogen oxide (NOx) in the measurement gas is detected in the following manner, using the NOx sensor constructed as described above. Initially, the external measurement gas is introduced into the buffer space 8 from the clogging-preventive space 14 formed at the distal end portion of the sensor element 2, through the slit-like first diffusion controlling passages 20 formed at the upper and lower portions of the first partition wall 18. The atmosphere thus introduced into the buffer space 8 is then introduced into the first internal space 10 through the slit-like second diffusion controlling passages 24 formed at the upper and lower portions of the second partition wall 22. The voltage of the variable power source 54 is controlled such that the electromotive force V0 of the oxygen-partial-pressure detecting cell 52 is held constant, so that a pumping current Ip0 of the main pumping cell 50 is controlled. In this respect, the oxygen partial pressure in the atmosphere in the first internal space 10 is controlled to a prescribed value, e.g., about $10^{-7}$ atm.

The atmosphere is then introduced from the first internal space 10 into the second internal space 12 through the slit-like third diffusion controlling passages 32 formed at the upper and lower portions of the third partition wall 30. The atmosphere thus introduced into the second internal space 12 is subjected to a pumping action by the auxiliary pumping cell 56 to pump oxygen in the atmosphere, with an electric power supplied from the variable power source 60 whose voltage is controlled on the basis of an electromotive force V1 detected by the oxygen-partial-pressure detecting cell 58. Thus, the oxygen partial pressure in the atmosphere in the second internal space 12 is controlled to a low value at which the measurement of the nitrogen oxide is not substantially influenced. The pumping current Ip1 of the auxiliary pumping cell 56 is fed, as a control signal, to the oxygen-partial-pressure detecting cell 52, whereby the electromotive force V0 of the same 52 is controlled. As a result, a gradient of the oxygen partial pressure in the atmosphere is held constant in the second internal space 12 between the third diffusion controlling passages 32 and the auxiliary pumping electrode 34.

The atmosphere in the second internal space 12 the oxygen partial pressure of which has been controlled reaches the measuring electrode 36 through the electrode-protective layer 38, under the prescribed diffusion resistance. The nitrogen oxide in the atmosphere which has reached the measuring electrode 36 is reduced or decomposed around the measuring electrode 36 to generate oxygen. The thus generated oxygen is pumped by the measurement pumping cell 62. In this instance, the voltage of the variable power source 66 is controlled such that an electromotive force V2 of the oxygen-partial pressure detecting cell 64 is held constant. Here, the amount of oxygen generated around the measuring electrode 36 is proportional to the concentration of the nitrogen oxide in the measurement gas. Accordingly, the concentration of the nitrogen oxide (NOx) in the desired measurement gas can be calculated based on the pumping current Ip2 of the measurement pumping cell 62.

In measuring the concentration of the NOx existing in the external measurement gas using the sensor element 2 constructed as described above, the oxygen partial pressure in the measurement gas introduced from the external measurement-gas space into the first internal space 10 is controlled to a constant value by a pumping action based on the pumping current Ip0 supplied to the main pumping cell 50. The controlled atmosphere in the first internal space 10 is then introduced into the second internal space 12, and the NOx in the atmosphere is reduced or decomposed by the measuring electrode 36. The oxygen generated by the reduction or the decomposition is pumped out from the second internal space 12 by the measurement pumping cell 62, whereby the pumping current Ip2 flowing through the measurement pumping cell 62 is detected. On the basis of the detected pumping current Ip2, the NOx concentration in the measurement gas is measured. The pumping current Ip2 flowing through the measurement pumping cell 62 varies among the NOx sensors each having the construction shown in FIGS. 1 and 2, and the different values of the pumping current Ip2 are recognized as variations in the sensor output among the individual NOx sensors.

In the light of the above, the sensor output of the NOx sensor is corrected in the following manner according to the present invention. Initially, the measurement of the NOx concentration is performed for a standard gas whose NOx concentration is already known, under a reference pressure on the basis of which the NOx concentration is obtained, using, as calibration sensors, an appropriate number of the NOx sensors each having the construction illustrated above, namely, a sufficient number of the NOx sensors to obtain the intended sensor-variation relational expression, whereby the pumping current Ip0 and the pumping current Ip2 are obtained for each of the calibrations sensors to calculate the Ip2/Ip0 value for each of the calibration sensors. Here, in general, an atmospheric pressure (1.0 bar) is employed as the reference pressure while a nitrogen-based gas containing about 100-1000 ppm of NOx is employed as the standard gas.

In the meantime, the measurement of the NOx concentration similar to that described above is performed on each of the plurality of or the multiplicity of calibration sensors under a specific pressure (p') of the standard gas different from the reference pressure, whereby a pumping current (NOx concentration output signal) $Ip2(p')$ flowing through the measurement pumping cell 62 is detected. While the specific pressure (p') is suitably selected so as to be held within a fluctuation range of the pressure of the measurement gas whose NOx concentration is to be measured, the specific pressure is generally held in a range of about 1.2-1.8 bar. Then by utilizing a pumping current (NOx concentration output signal) $Ip2(p_0)$ flowing through the measurement pumping cell 62 that is obtained in the NOx concentration measurement for the standard gas under the reference pressure, there is calculated for each of the calibration sensors, as an output change percentage, a ratio of change of the pumping current $Ip2(p')$ flowing through the measurement pumping cell 62 under the specific pressure, to the pumping current $Ip2(p_0)$, namely, there is calculated a value $[Ip2(p')-Ip2(p_0)]/Ip2(p_0)$.

Figure 3:
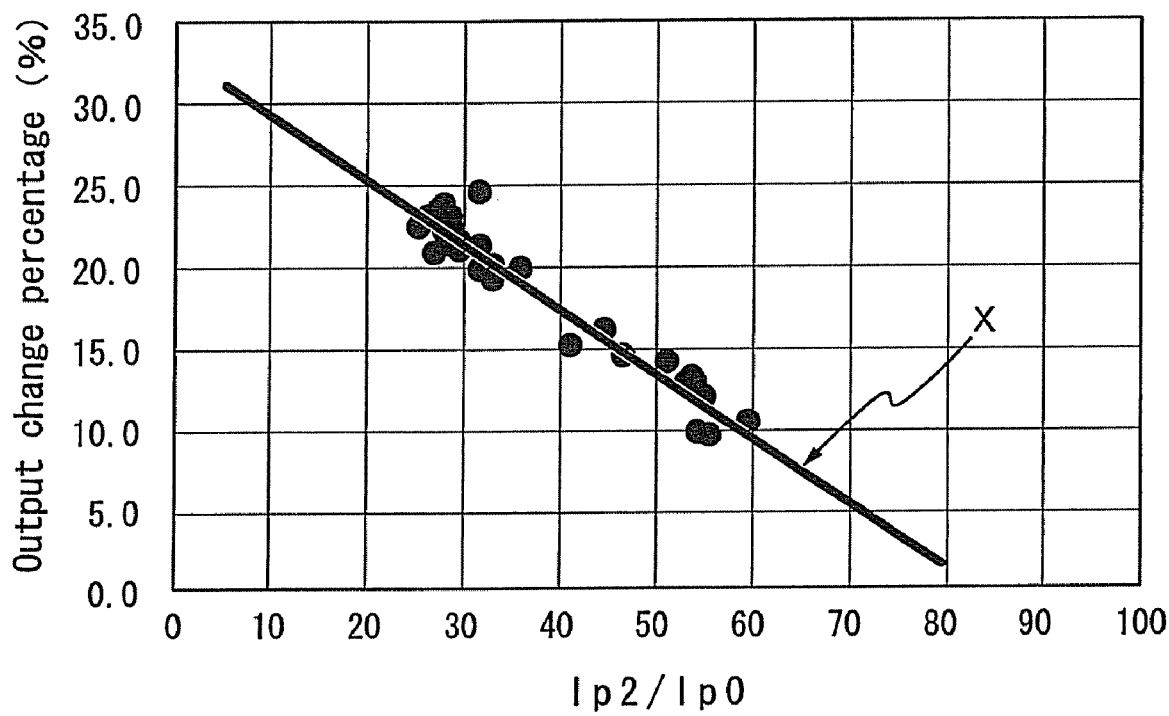
FIG. 3 shows a graph in which is plotted the relationship between the IP2/Ip0 value and the output change percentage obtained in Example 1 for each of calibrations sensors and also shows a sensor-variation relational line obtained from the relationship.

On the basis of a relationship between the Ip2/Ip0 value and the output change percentage $[=\{Ip2(p_0)\}/Ip2(p')]$ obtained for each of the calibration sensors, the sensor-variation relational expression is obtained. More specifically explained with reference to FIG. 3, the relationship between the Ip2/Ip0 value and the output change percentage for each calibration sensor is plotted on one graph so as to obtain the sensor-variation relational expression (X). In the present embodiment, the sensor-variation relational expression (X) is obtained as a linear expression and is indicated by a straight line.

In the present invention, the linear expression is advantageously obtained as the sensor-variation relational expression (X) on the basis of the relationship between the Ip2/Ip0 value and the output change percentage for each of the calibration sensors, and the output change percentage that corresponds to a change in the Ip2/Ip0 value is linearly indicated. The sensor-variation relational expression may be indicated by a quadratic expression or a multi-degree expression which represent a curve. Further, the sensor-variation relational expression may be obtained using a suitable data processing device, simply on the basis of the relationship between the Ip2/Ip0 value and the output change percentage for each calibration sensor, without performing plotting shown in FIG. 3.

Subsequently, there are measured a pumping current Ip2 and a pumping current Ip0 for a subject NOx sensor which is different from the above-indicated calibration sensors but has a construction similar to that of each calibration sensor and whose output is to be corrected, and an output change percentage β that corresponds to an Ip2/Ip0 value is obtained according to the sensor-variation relational expression (X) obtained as described above. The Ip2/Ip0 value can be easily calculated utilizing the pumping current values Ip2 and Ip0 which are obtained for each of all of the produced NOx sensors including the subject NOx sensor in the NOx concentration measurement using the above-indicated standard gas under the reference pressure. The output change percentage β that corresponds to the Ip2/Ip0 value is obtained from the sensor-variation relational expression, more specifically, from the sensor-variation relational line (straight line) indicated by the graph of FIG. 3.

By utilizing the output change percentage β obtained as described above, there is calculated, according to the above-indicated formula (I), a pressure correction coefficient α for performing output correction on the subject NOx sensor based on the above-indicated formula (II). That is, by utilizing the output change percentage β determined as described above, a relationship between a pumping current $Ip2(p)$ for the measurement gas under a prescribed pressure (p) and a pumping current $Ip2(p_0)$ for the measurement gas under the reference pressure $(p_0)$ is represented as follows: $Ip2(p) = Ip2(p_0) \times (1+\beta)$. This relationship is introduced into the above-indicated formula (II) which is a known empirical formula representing a relationship of sensor output with respect to pressure, so that the above-indicated formula (I) is derived.

The thus obtained pressure correction coefficient α takes account of variations among the individual NOx sensors. The NOx concentration in the measurement gas is actually measured using the subject NOx sensor to detect the pumping current $Ip2(p)$ flowing through the measurement pumping cell 62 while the pressure p of the measurement gas is detected. By substituting the obtained pumping current $Ip2(p)$ and pressure p into the above-indicated formula (II), together with the pressure correction coefficient α obtained as described above, the pumping current $Ip2(p_0)$ flowing through the measurement pumping cell 62 under the reference pressure $p_0$ is obtained by calculation. The thus calculated pumping current $Ip2(p_0)$ is utilized as a value indicative of the actual NOx concentration in the measurement gas, so that the output correction on the subject NOx sensor can be effectively performed. Further, the output correction takes account of the variations among the individual sensors, thereby ensuring more accurate sensor output.

As the NOx sensor used in the sensor output correction in accordance with the pressure of the measurement gas, various known NOx sensors may be employed in addition to the NOx sensor equipped with the sensor element 2 having the illustrated structure, provided that the NOx sensor is configured to detect the pumping current Ip0 supplied to the main oxygen pumping means (50) and to detect the pumping current Ip2 flowing through the measurement oxygen pumping means

(62) according to the present invention. While the measuring electrodes (28, 26, 34, 36) in the respective sensor cells (68, 52, 58, 64) function also as the pumping electrodes of the respective pumping cells (50, 56, 62) in the illustrated sensor element 2, the measuring electrodes may be constituted by other electrodes separate from the pumping electrodes. Further, while the reference-gas space and the reference electrode are common to the sensor cells as illustrated above, the reference-gas space and the reference electrode may be provided by other spaces and other electrodes respectively provided for the individual sensor cells.

While the sensor element 2 according to the illustrated embodiment has the clogging-preventive space 14 formed between the gas inlet 16 and the first partition wall 18, the clogging-preventive space 14 may be eliminated. Instead of providing the clogging-preventive space 14, the first partition wall 18 may be formed such that the inlet ends of the respective first diffusion controlling passages 20 are located at the gas inlet 16. Further, the configurations of the second and third diffusion controlling passages 24, 32 may not be limited to those in the illustrated embodiment.

In calculating the pumping current $Ip2(p_0)$ using the above-indicated formula (II), the pressure p of the measurement gas needs to be detected. For detecting the pressure, a pressure sensor separate from the NOx sensor is used to measure the pressure p of the measurement gas. Any known pressure sensor may be used.

Further, a computing unit such as a computer may be advantageously employed in the data processing of the invention such as the calculation of the Ip2/Ip0 value based on the pumping current values Ip2, Ip0 obtained for each of the calibration sensors and the subject NOx sensor, the calculation of the output change percentage for each of the calibration sensors, the derivation of the sensor-variation relational expression, the calculation of the output change percentage $\beta$ and the pressure correction coefficient $\alpha$ for the subject NOx sensor, the calculation of the pumping current $Ip2(p_0)$ in the subject NOx sensor.

While there has been explained in detail one embodiment of the method of correcting NOx sensor output according to the present invention taking a representative NOx sensor as an example, it is to be understood that the present invention is not limited to the illustrated embodiment and that the present invention may be embodied with various changes, modifications, and improvements, which may occur to those skilled in the art, without departing from the spirit of the invention.

EXAMPLES

Hereinafter, representative examples of the present invention will be described to further clarify the invention. It is to be understood that the invention is not limited to the details of the examples.

Example 1

Initially, there were prepared a large number of NOx sensors each having the sensor element (2) constructed as shown in FIGS. 1 and 2. By using the prepared NOx sensors, the NOx concentration and the oxygen concentration were measured for a standard gas having the NOx (nitrogen oxide) concentration of 500 ppm and the oxygen concentration of 18% under the reference pressure of 1.0 bar (atmospheric pressure) and under the specific pressure of 1.5 bar which is higher than the reference pressure by 0.5 bar. For each of the NOx sensors, the pumping current values $Ip0[=Ip0(p_0)]$, $Ip0(p')$ flowing through the main pumping cell (50) and the pumping current values $Ip2[=Ip2(p_0)]$, $Ip2(p')$ flowing through the measurement pumping cell (62) were measured. Further, the Ip2/Ip0 value and the output change percentage $[Ip2(p')-Ip2(p_0)]/Ip2(p_0)$ were calculated for each of the NOx sensors. The relationship between the Ip2/Ip0 value and the output change percentage obtained for each NOx sensor was plotted on one graph to obtain a graph shown in FIG. 3, and there was obtained from the graph a sensor-variation relational line X (i.e., a sensor-variation relational expression represented by a linear expression) which estimates output variations among the NOx sensors.

Subsequently, by using a subject NOx sensor A whose output is to be corrected and which is different from the calibration sensors used for obtaining the above-indicated sensor-variation relational line X but is identical in construction with the calibration sensors, the NOx concentration of the above-indicated standard gas (having the NOx concentration of 500 ppm and the oxygen concentration of 18%) under the reference pressure (1.0 bar) was measured to detect the pumping current Ip0 of the main pumping cell (50) and the pumping current Ip2 of the measurement pumping cell (62). Based on the detected Ip0, Ip2, the Ip2/Ip0 value was calculated. The calculated Ip2/Ip0 value is equal to 43. Then the output change percentage $\beta$ that corresponds to the calculated Ip2/Ip0 value was obtained from the sensor-variation relational line X shown in FIG. 3. The obtained output change percentage $\beta$ is equal to 16.1% (=0.161).

The thus obtained output change percentage $\beta$ (=0.161) is substituted in the above-indicated formula (I) and the pressure correction coefficient $\alpha$ is calculated from the formula (I) when the reference pressure $p_0$ is equal to 1.0 bar and the specific pressure p' of the standard gas is equal to 1.5 bar. The calculated pressure correction coefficient $\alpha$ is equal to 0.42

The subject NOx sensor A for which the pressure correction coefficient $\alpha$ was thus obtained is installed on an exhaust pipe of an experimental engine bench (a diesel engine with a 2.5 L turbocharger), and the concentration of NOx contained in an exhaust gas (as a measurement gas) passing through the exhaust pipe was measured for each of prescribed engine rotation conditions (rotational speed/torque). Further, in order to accurately obtain the NOx concentration in the exhaust gas, the NOx concentration was detected separately using an analyzer while at the same time the pressure of the exhaust gas at each of measurement points was detected by a commercially available pressure sensor. The NOx concentration was measured under the following engine operating conditions. The engine rotational speed is in a range from idle to 3500 rpm. The temperature of the exhaust gas is in a range of 80-700 C°. The oxygen concentration in the exhaust gas is in a range of 1-17%. The NOx sensor A was disposed at a position downstream of an exhaust manifold of the engine by a distance of 1 m.

Each measured value (actually measured value) obtained in a case where the exhaust gas having different NOx concentrations is used as the measurement gas is utilized as a value $Ip2(p)$ and substituted into the above-indicated formula (II). Further, the value $\alpha$ (=0.42) obtained as described above and the gas pressure p detected by the pressure sensor are also substituted in the formula (II), thereby calculating the pumping current $Ip2(p_0)$ flowing through the measurement cell (62) under the reference pressure ($p_0$=1.0 bar) for each measuring point. The results represented as the NOx concentration are indicated in the following TABLE 1.

TABLE 1

| | Measurement | | | | | | | |
|---|---|---|---|---|---|---|---|---|
| | 1 | 2 | 3 | 4 | 5 | 6 | 7 | 8 |
| Rotational speed/torque [rpm/Nm] | 750/IDLE | 1000/5 | 1000/15 | 1500/5 | 1500/15 | 2000/20 | 2500/20 | 3500/20 |
| Gas pressure (bar) | 1.003 | 1.008 | 1.018 | 1.016 | 1.027 | 1.065 | 1.140 | 1.298 |
| NOx value detected by analyzer [ppm] | 84 | 123 | 234 | 122 | 271 | 319 | 336 | 387 |
| Actually measured NOx value [ppm] | 84 | 123 | 232 | 125 | 273 | 329 | 356 | 428 |
| Corrected NOx value [ppm] | 84 | 123 | 231 | 124 | 270 | 321 | 338 | 387 |
| Deviation (1) [ppm] | 0 | 0 | −2 | 3 | 2 | 10 | 20 | 41 |
| Deviation (2) [ppm] | 0 | 0 | −3 | 2 | −1 | 2 | 2 | 0 |

Deviation (1) = Actually measured NOx value − NOx value detected by analyzer
Deviation (2) = Corrected NOx value − NOx value detected by analyzer In the above TABLE 1, for each measuring point, there are shown both of the deviation (=the actually measured NOx value−the NOx value detected by the analyzer) in an instance where the sensor output correction in accordance with the pressure of the measurement gas was not performed and the deviation (=the corrected NOx value−the NOx value detected by the analyzer) in an instance where the sensor output correction in accordance with the pressure of the measurement gas was performed. As apparent from the results indicated in the above TABLE 1, the NOx concentration close to that detected by the analyzer can be obtained by performing the sensor output correction according to the present invention. It is thus recognized that the accuracy of measuring the NOx concentration is advantageously improved.

Subsequently, by using the subject NOx sensor B whose output is to be corrected and for which the pressure correction coefficient α was obtained, the NOx concentration in the exhaust gas of the diesel engine was measured for each of the prescribed engine rotation conditions (rotational speed/torque) as in the Example 1. Further, the gas pressure at each measuring point was measured, and the true NOx concentration was also measured using the analyzer. The measured values are indicated in the following TABLE 2. In addition, on the basis of the actually measured NOx values under the respective gas pressure values (p), the output correction using the formula (II) according to the invention was performed, and the results thereof are also indicated in TABLE 2.

TABLE 2

| | Measurement | | | | | | | |
|---|---|---|---|---|---|---|---|---|
| | 1 | 2 | 3 | 4 | 5 | 6 | 7 | 8 |
| Rotational speed/torque [rpm/Nm] | 750/IDLE | 1000/5 | 1000/15 | 1500/5 | 1500/15 | 2000/20 | 2500/20 | 3500/20 |
| Gas pressure (bar) | 1.004 | 1.009 | 1.018 | 1.017 | 1.027 | 1.065 | 1.142 | 1.302 |
| NOx value detected by analyzer [ppm] | 78 | 117 | 235 | 118 | 266 | 317 | 349 | 404 |
| Actually measured NOx value [ppm] | 88 | 131 | 241 | 128 | 268 | 325 | 372 | 446 |
| Corrected NOx value [ppm] | 87 | 130 | 239 | 127 | 265 | 317 | 353 | 403 |
| Deviation (1) [ppm] | 10 | 14 | 6 | 10 | 2 | 8 | 23 | 42 |
| Deviation (2) [ppm] | 9 | 13 | 4 | 9 | −1 | 0 | 4 | −1 |

Deviation (1) = Actually measured NOx value − NOx value detected by analyzer
Deviation (2) = Corrected NOx value − NOx value detected by analyzer As apparent from the results indicated in the above TABLE 2, the corrected NOx values obtained by performing, on the corresponding actually measured NOx values, the output correction according to the invention are closer to the corresponding NOx values detected by the analyzer which are close to the actual NOx values in the exhaust gas. It is thus recognized that the accuracy of measuring the NOx concentration is advantageously improved.

Example 2

As in the Example 1, the measurement of the NOx concentration was performed for the standard gas under the reference pressure, using a NOx sensor B which is different from the subject NOx sensor A used in the Example 1 but is identical in construction with the NOx sensor A, to detect the pumping current values Ip0, Ip2. On the basis of the detected Ip0, Ip2, the Ip2/Ip0 value was calculated. The calculated Ip2/Ip0 value is equal to 42. The output change percentage β that corresponds to the calculated Ip2/Ip0 value was obtained from the sensor-variation relational line X shown in the graph of FIG. 3. The obtained output change percentage β is equal to 16.4% (=0.165). Further, on the basis of the thus obtained output change percentage β, the pressure correction coefficient α is calculated according to the formula (I) of to the invention. The calculated pressure correction coefficient α is equal to 0.42 where $p_0$=1.0 bar and p'=1.5 bar.

Example 3

Measured NOx values are evaluated as in the Example 1 for another NOx sensor C which is identical in construction with the calibration sensors used in the Example 1 and which is different from the subject NOx sensors A, B evaluated in the Example 1 and the Example 2.

More specifically explained, as in the Example 1, the Ip2/Ip0 value was obtained in the measurement of the NOx concentration using the standard gas for the subject NOx sensor C. The output change percentage β that corresponds to the obtained Ip2/Ip0 value was then obtained from the sensor-variation relational line X shown in FIG. 3. The obtained output change percentage β is equal to 18.1% (=0.181). Further, on the basis of the thus obtained output change percentage β, the pressure correction coefficient α was calculated according to the formula (I) of the invention. The calculated pressure correction coefficient α is equal to 0.46.

Subsequently, the NOx concentration in the exhaust gas of the diesel engine was measured using the subject NOx sensor C whose output is to be corrected. The results are indicated in the following TABLE 3. As apparent from the results indicated in TABLE 3, it is recognized that the corrected NOx values obtained by performing the output correction according to the invention are close to the corresponding true NOx values detected by the analyzer.

TABLE 3

| | Measurement | | | | | | | |
|---|---|---|---|---|---|---|---|---|
| | 1 | 2 | 3 | 4 | 5 | 6 | 7 | 8 |
| Rotational speed/torque [rpm/Nm] | 750/IDLE | 1000/5 | 1000/15 | 1500/5 | 1500/15 | 2000/20 | 2500/20 | 3500/20 |
| Gas pressure (bar) | 1.003 | 1.009 | 1.015 | 1.015 | 1.026 | 1.067 | 1.140 | 1.293 |
| NOx value detected by analyzer [ppm] | 79 | 120 | 237 | 125 | 270 | 321 | 354 | 406 |
| Actually measured NOx value [ppm] | 84 | 131 | 240 | 132 | 274 | 330 | 377 | 446 |
| Corrected NOx value [ppm] | 83 | 130 | 238 | 131 | 271 | 321 | 356 | 400 |
| Deviation (1) [ppm] | 5 | 11 | 3 | 7 | 4 | 9 | 23 | 40 |
| Deviation (2) [ppm] | 4 | 10 | 1 | 6 | 1 | 0 | 2 | −6 |

Deviation (1) = Actually measured NOx value − NOx value detected by analyzer
Deviation (2) = Corrected NOx value − NOx value detected by analyzer

What is claimed is:

1. A method of correcting an output of a NOx sensor configured to measure a NOx concentration in a measurement gas, by controlling, to a constant value, an oxygen partial pressure in the measurement gas introduced into a first internal space from a measurement-gas space owing to a pumping action based on a pumping current Ip0 supplied to main oxygen pumping means, introducing a controlled atmosphere in the first internal space into a second internal space for reduction or decomposition of NOx in the atmosphere, and pumping out oxygen generated upon the reduction or the decomposition from the second internal space by measurement oxygen pumping means, so as to measure the NOx concentration in the measurement gas based on a pumping current Ip2 flowing through the measurement oxygen pumping means, the method comprising:

a first step of obtaining a sensor-variation relational expression, wherein: the pumping current Ip0 and the pumping current Ip2 are measured for an appropriate number of the NOx sensors each as a calibration sensor using a standard gas, under a reference pressure, whose NOx concentration is already known, for calculating an Ip2/Ip0 value for each of the calibration sensors; an output change percentage is calculated as a ratio of change of a pumping current flowing through the measurement oxygen pumping means obtained in each of the calibration sensors using the standard gas under a prescribed specific pressure different from the reference pressure, to a pumping current flowing through the measurement oxygen pumping means obtained in each of the calibration sensors using the standard gas under the reference pressure; and the sensor-variation relational expression is obtained from a relationship between the Ip2/Ip0 value and the output change percentage for said each of the calibration sensors;

a second step of obtaining an output change percentage β for a subject NOx sensor which is different from the calibration sensors and whose output is to be corrected, by calculating, for the subject NOx sensor, the Ip2/Ip0 value using the standard gas under the reference pressure so as to obtain, from the sensor-variation relational expression, the output change percentage β that corresponds to the calculated Ip2/Ip0 value;

a third step of calculating a pressure correction coefficient α based on the output change percentage β obtained in the second step, according to the following formula (I):

$$\alpha(p'-p_0)/p' = \beta/(\beta+1) \quad (I)$$

wherein $p_0$ represents the reference pressure and p' represents the specific pressure of the standard gas; and a fourth step of performing output correction on the subject NOx sensor, wherein: a NOx concentration in the measurement gas is measured using the subject NOx sensor to detect a pumping current Ip2(p) flowing through the measurement oxygen pumping means while a pressure p of the measurement gas is detected; and a pumping current Ip2($p_0$) flowing through the measurement oxygen pumping means under the reference pressure $p_0$ is calculated based on the pumping current Ip2(p) and the pressure p, according to the following formula (II):

$$[Ip2(p_0) - Ip2(p)]/Ip2(p) = \alpha(p_0 - p)/p \quad (II)$$

so as to perform the output correction on the subject NOx sensor.

2. The method according to claim 1, wherein the sensor-variation relational expression in the first step is obtained as a linear expression.

3. The method according to claim 1, wherein the reference pressure is an atmospheric pressure.

4. The method according to claim 1, wherein the standard gas contains the NOx in concentrations of from 100 ppm to 1000 ppm.

5. The method according to claim 1, wherein the specific pressure is a pressure that falls within a pressure fluctuation range of the measurement gas.

6. The method according to claim 1, wherein each of the main oxygen pumping means and the measurement oxygen pumping means is constituted by an electrochemical cell including a solid electrolyte and a pair of electrodes disposed adjacent thereto.

7. The method according to claim 1, wherein the NOx sensor includes a sensor element in which the main oxygen pumping means and the measurement oxygen pumping means are provided integrally with the first and second internal spaces.

8. The method according to claim 1, wherein the measurement oxygen pumping means includes: an inner pumping electrode which is formed inside of the second internal space and which reduces or decomposes the NOx contained in the atmosphere introduced from the first internal space, as a result of contact with the atmosphere; and an outer pumping electrode formed outside of the second internal space, the measurement oxygen pumping means performing a pumping action with respect to oxygen generated by reduction or decomposition of the NOx contained in the atmosphere introduced from the first internal space, based on a pumping current flowing between the inner and outer pumping electrodes.

9. The method according to claim 8, wherein the inner pumping electrode formed in the second internal space is covered with a porous layer formed thereon, and an atmosphere in the second internal space is brought into contact with the inner pumping electrode through the porous layer under a prescribed diffusion resistance.

10. The method according to claim 1, wherein the NOx sensor is provided with an auxiliary oxygen pumping means which includes a pair of auxiliary pumping electrodes respectively formed inside and outside of the second internal space, the auxiliary oxygen pumping means performing a pumping action with respect to oxygen contained in the atmosphere introduced from the first internal space, based on an auxiliary pumping current flowing between the pair of auxiliary pumping electrodes.

11. The method according to claim 10, wherein the auxiliary oxygen pumping means is constituted by an electrochemical cell in which the pair of auxiliary pumping electrodes are formed on a solid electrolyte.

12. The method according to claim 10, wherein the NOx sensor includes a sensor element in which the auxiliary oxygen pumping means is provided integrally with the main oxygen pumping means, the measurement oxygen pumping means, and the first and second internal spaces.

* * * * *